United States Patent
Butler

(10) Patent No.: US 9,138,547 B2
(45) Date of Patent: Sep. 22, 2015

(54) METHOD AND APPARATUS FOR ELECTRICALLY DESTROYING A SYRINGE NEEDLE OF A PEN-TYPE HYPODERMIC SYRINGE

(71) Applicant: Q Care International LLC, Marietta, GA (US)

(72) Inventor: William F. Butler, Marietta, GA (US)

(73) Assignee: Q CARE INTERNATIONAL LLC, Marietta, GA (US)

( * ) Notice: Subject to any disclaimer, the term of this patent is extended or adjusted under 35 U.S.C. 154(b) by 400 days.

(21) Appl. No.: 13/713,289

(22) Filed: Dec. 13, 2012

(65) Prior Publication Data

US 2014/0166624 A1    Jun. 19, 2014

(51) Int. Cl.
*B23H 9/00* (2006.01)
*A61M 5/32* (2006.01)

(52) U.S. Cl.
CPC ............ *A61M 5/3278* (2013.01); *A61M 5/3205* (2013.01); *A61M 2005/3283* (2013.01); *Y10T 83/222* (2015.04); *Y10T 83/728* (2015.04)

(58) Field of Classification Search
CPC ............. B23H 9/00; B23H 9/001; B23H 3/00
USPC ......... 219/68, 69.1, 67, 69.11, 69.17; 83/944, 83/165
See application file for complete search history.

(56) References Cited

U.S. PATENT DOCUMENTS

| | | | |
|---|---|---|---|
| 4,565,311 A * | 1/1986 | Pugliese et al. | 225/94 |
| 5,391,849 A * | 2/1995 | Furuya et al. | 219/68 |
| 5,468,928 A * | 11/1995 | Yelvington | 219/68 |
| 5,736,706 A * | 4/1998 | Butler | 219/68 |
| 6,169,259 B1 * | 1/2001 | Hall et al. | 219/68 |
| 6,621,031 B2 * | 9/2003 | Stevens | 219/69.1 |
| 2004/0210192 A1 * | 10/2004 | Degentesh et al. | 604/151 |
| 2005/0072758 A1 * | 4/2005 | Jackson et al. | 219/68 |
| 2006/0184157 A1 * | 8/2006 | Spohn et al. | 604/535 |
| 2007/0016145 A1 * | 1/2007 | Berler | 604/240 |
| 2007/0260194 A1 * | 11/2007 | Nemoto et al. | 604/228 |
| 2008/0125713 A1 * | 5/2008 | Nemoto et al. | 604/152 |
| 2009/0068066 A1 * | 3/2009 | Hoffman et al. | 422/100 |
| 2010/0234856 A1 * | 9/2010 | Stoianovici et al. | 606/130 |
| 2010/0316526 A1 * | 12/2010 | Chandrasekhar | 422/21 |
| 2013/0334175 A1 * | 12/2013 | Jackson et al. | 219/68 |

\* cited by examiner

*Primary Examiner* — Dana Ross
*Assistant Examiner* — Michael Laflame, Jr.
(74) *Attorney, Agent, or Firm* — McClure, Qualey & Rodack, LLP

(57) ABSTRACT

A method and apparatus for sterilizing and destroying a syringe needle includes a rotating needle carriage that receives a needle in a loading position. The needle carriage includes a port sized to accept a pen-type hypodermic syringe and an insert to downsize the port for accepting a conventional hypodermic syringe. The needle carriage is rotated downwardly to a cut-off position. At the cut-off position, two opposing contact blades pinch the needle, which electrically connects the positive and negative terminals of a battery. Current flows through the contact blades to shear the needle. The sheared portion of the needle then falls into a waste compartment in the bottom of the apparatus. When the syringe is removed from the needle carriage, the needle carriage rotates upwardly and returns to the loading position.

22 Claims, 13 Drawing Sheets

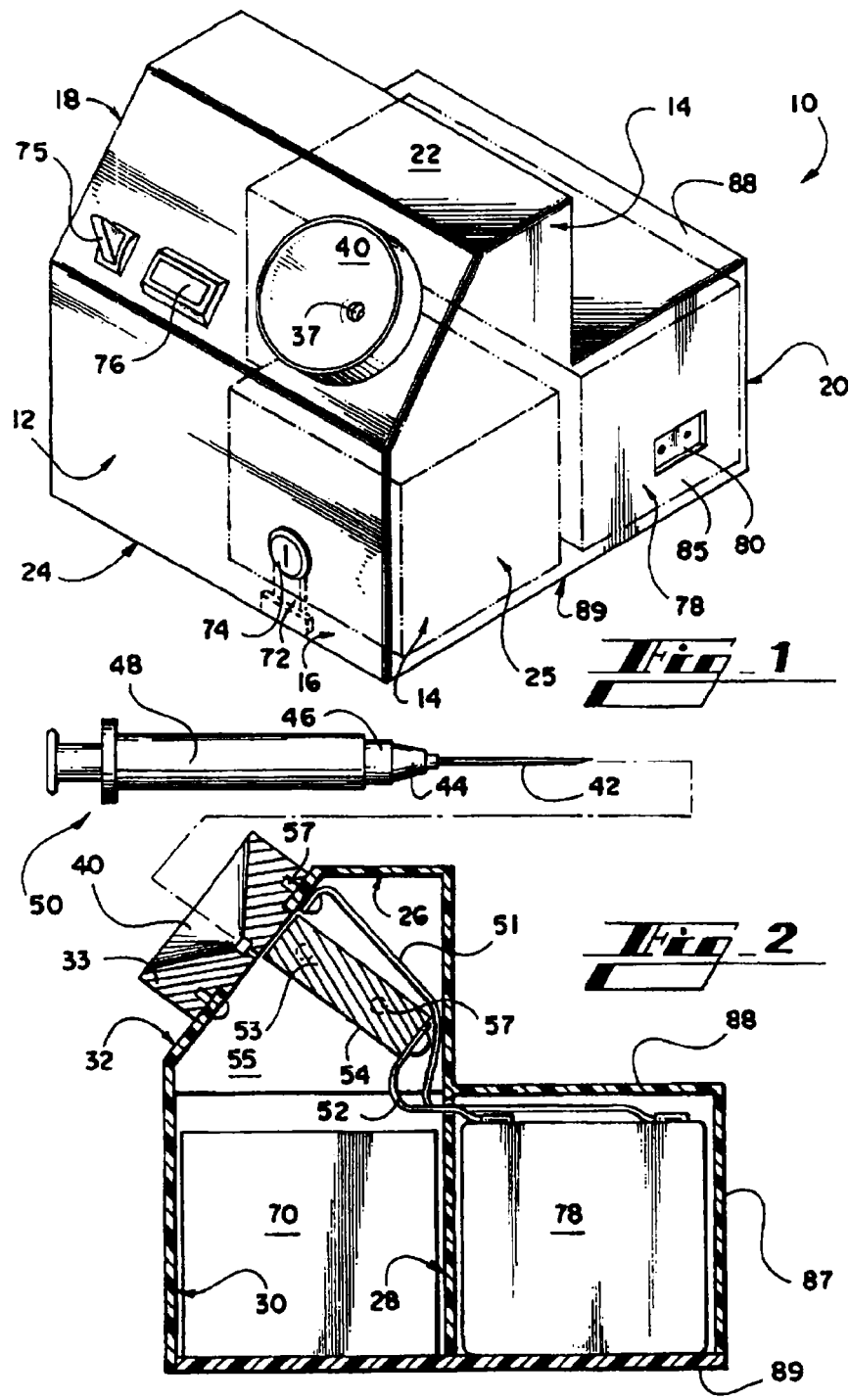
Prior Art

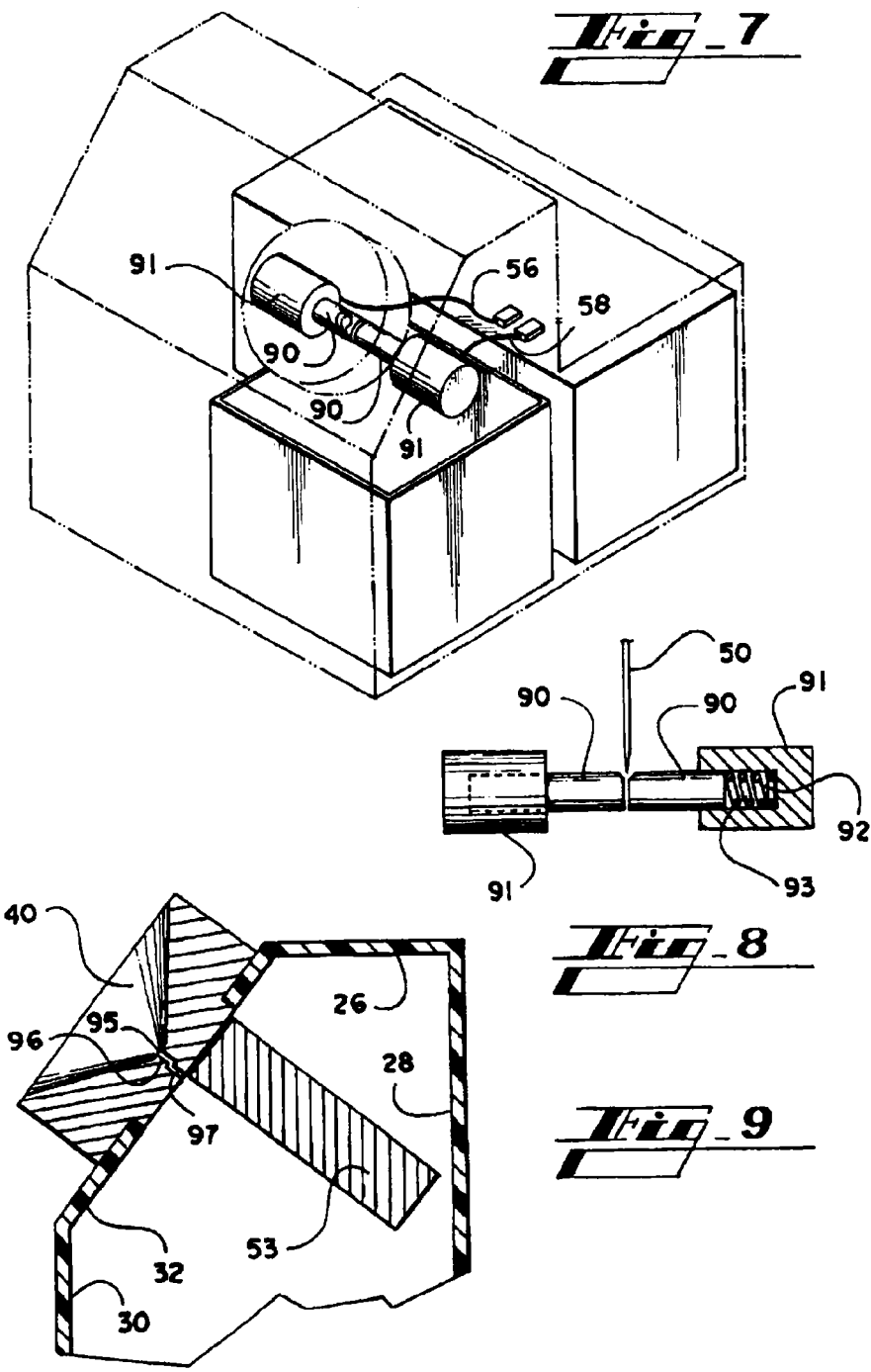
Prior Art

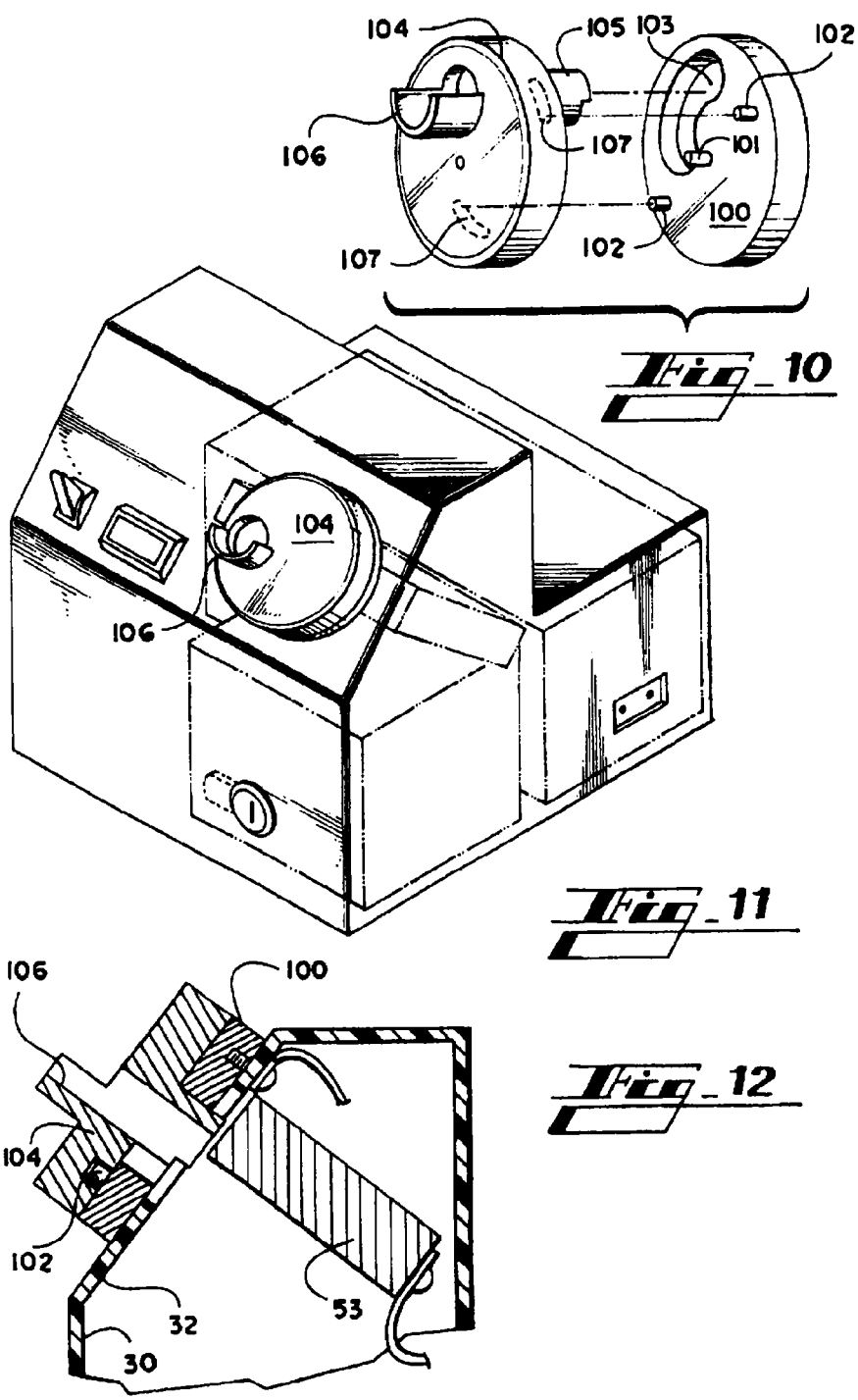
Prior Art

Loading Position

Prior Art

Cut-Off Position

Prior Art

METHOD AND APPARATUS FOR ELECTRICALLY DESTROYING A SYRINGE NEEDLE OF A PEN-TYPE HYPODERMIC SYRINGE

TECHNICAL FIELD

This invention relates to a method and apparatus for destroying the needle portion of a syringe. In particular, the present invention relates to a method and apparatus that heats, sterilizes and severs the needle portion of a pen-type hypodermic syringe after the needle has been used on a patient.

BACKGROUND OF THE INVENTION

The threat of infectious diseases, in particular AIDS and hepatitis B, is very prevalent today in hospitals and doctors' offices as a result of the use of hypodermic syringes. The Centers for Disease Control in Atlanta has extensively studied accidental syringe sticking incidents and have logged where most of the accidents occur and to whom. The Centers' records indicate that nurses experience more incidents than most other medical personnel.

Recovering the needle with the plastic tip cover provided with the syringe after use has not solved the problem because the cover can slip off or a person can be stuck by merely attempting to place the cover on the needle. Other means presently utilized for the disposal of used syringes still leave the steel of the hypodermic needle on the syringe, thereby exposing the waste handlers to the possibility of being pricked. The present syringe disposal systems are also very expensive.

The prior art includes the apparatus disclosed in U.S. Pat. No. 4,628,169 which describes an apparatus for melting only the tip of the needle, with the remainder of the metal on the syringe being detached by a separate operation. The remaining metal portion may still be contaminated. That system still leaves the possibility of the person collecting the remaining needle portion being exposed to microorganisms. Also, any infectious fluids are still available to flow out of the now-open plastic portion of the syringe.

U.S. Pat. No. 4,877,934 discloses a needle destroying apparatus which utilizes converging electrodes. The hypodermic syringe is inserted into the apparatus in a vertical orientation and is either slid onto a bottom electrode ramp or an electrode that can slide toward the bottom electrode thereby destroying the needle. However, because of the vertical orientation of the needle as it is inserted into the apparatus, the burnt needle tends to bend away from the ramp and loses contact with the bottom electrode. In addition, because of the vertical orientation, the burnt needle tends to collect on the bottom electrode thereby fouling the surface of the bottom electrode.

U.S. Pat. No. 5,736,706 teaches a device that both melts the needle and shears the needle portion from the syringe. This particular patent is commonly owned with the present application and shares some of the same features. It does not, however, accept the newer generation of pen-type hypodermic syringes.

What is needed is a needle destruction apparatus that is easy to operate and will reliably and efficiently destroy the needle of a pen-type hypodermic syringe. What is further needed is an apparatus that can be used in the clinic that can be used for long periods of time before it has to be taken apart and cleaned. An apparatus is needed that will treat used syringes to prevent storage of live viruses and other microorganisms in unsealed containers at room temperature, causing unwanted aerosol vapor to contaminate room air breathed by health care workers and patients.

SUMMARY OF THE INVENTION

The present invention is an apparatus for destroying a syringe needle comprising a housing and a rotating needle carriage that receives a needle in a loading position. The needle carriage is rotated downwardly to a cut-off position. At the cut-off position, two opposing contact blades pinch the needle which electrically connects the positive and negative terminals of a battery. Current flows through the contact blades and the needle, thereby melting the needle. A slight further rotation of the needle carriage causes the contact blades to sever a portion of the needle. The severed portion of the needle then falls into a waste compartment in the bottom of the housing. When the remainder of the needle is removed from the needle carriage, the needle carriage rotates upwardly and returns to the loading position.

It is, therefore, an object of the present invention to provide a safe, low cost, efficient and easy to use device for sterilizing and destroying the metal needle of a hypodermic syringe, thereby killing any infectious microorganism that may be present in or on the needle.

BRIEF DESCRIPTION OF THE DRAWINGS

FIG. 1 is a perspective view of the present invention;

FIG. 2 is a side view in partial cross-section of the device of FIG. 1;

FIG. 7 is a perspective view of a second alternative embodiment of the present invention;

FIG. 8 is an enlarged view of a portion of the device of FIG. 7;

FIG. 9 is a cross-sectional view of a third alternative embodiment of the present invention;

FIG. 10 is an enlarged exploded view of a portion of the device of FIG. 11;

FIG. 11 is a perspective view of a fourth alternative embodiment of the present invention;

FIG. 12 is a cross-sectional view of the device of FIG. 11;

DETAILED DESCRIPTION

Figure 3:
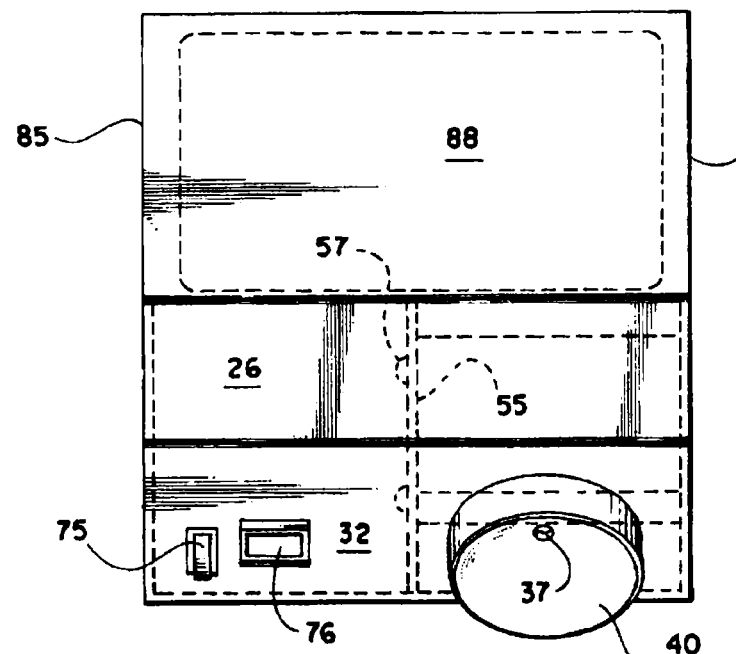
FIG. 3 is a top view of the device of FIG. 1.
Figure 4:
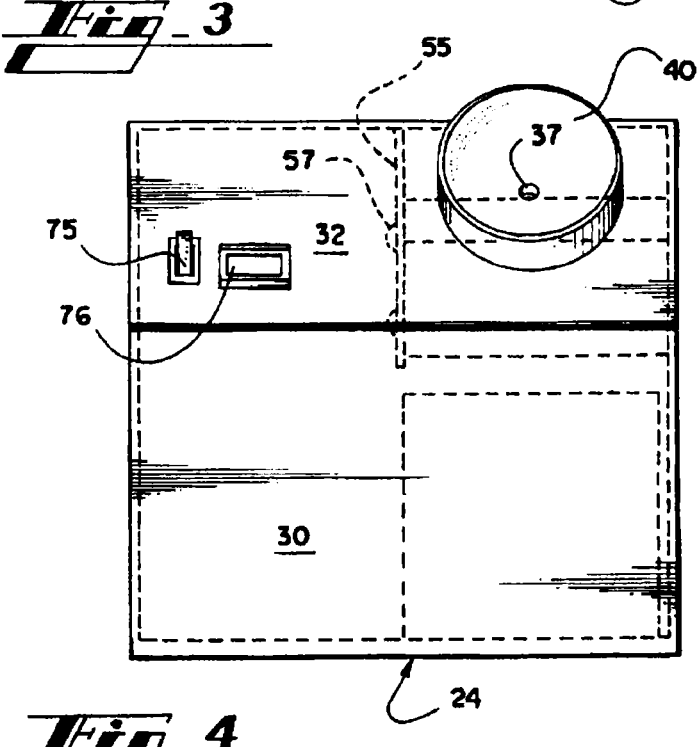
FIG. 4 is a front view of the device of FIG. 1.

The present invention is a method and apparatus for destroying the needle portion of a hypodermic syringe. The present invention is, in part, an apparatus that is capable of simultaneously sterilizing and destroying the needle portion of a hypodermic syringe and thereby eliminating the risk of infection by a microorganism that may be present in or on the needle.

When a syringe is inserted into the apparatus described herein, the needle is heated to a temperature of at least 1750° C. This temperature is capable of inactivating any virus, bacteria, yeast or other microorganism. In addition to being heated, the needle is melted so that it is removed from the remaining portion of the syringe. The nub remaining after the needle is melted and sealed so that no fluid can leak from the syringe.

Referring now to FIGS. 1 through 4, the numeral 10 denotes generally the present invention which comprises a housing 12, a burning chamber 14, and waste collection means 16. The housing 12 can be made of any suitable material such as metal, plastic or the like so long as the material is capable of maintaining structural integrity if exposed to sparks caused by the melting needle. The housing 12 is generally defined with side surfaces 18, end surfaces 20, a top surface 22, and a bottom surface 24. It is to be understood that the apparatus according to the present invention can be mounted to a wall or a surface such as the bottom of a wall cabinet or set on a counter.

The burning chamber 14 occupies the forward end of the housing 12 and preferably is constructed of a heat resistant material. The burning chamber 14 is defined by side chamber walls 25, a chamber top 26, rear chamber wall 28, front chamber wall 30 and a preferably non-vertical front face wall 32. A first electrical contact 33 is mounted on the front face wall 32. As seen more clearly in FIG. 2, the first electrical contact 33 is a conical shaped port 40 which is mounted to the front face wall 32 of the burning chamber 14 by means of screws 5. The first electrical contact 33 is connected by wire 51 to a battery 78. The port 40 tapers downwardly in the outer center surface and has an opening 37 disposed therethrough. The port 40 and opening 37 are dimensional to receive the metal needle portion 42, the neck portion 44, shoulder portion 46, and body portion 48 of a hypodermic needle 50.

A second electrical contact is a block 53 mounted within the burning chamber 14 to the rear chamber wall 28 and top 26 by means of mounting brackets 55 and screws 57. The block 53 is rectangular in shape with its lower surface 54 aligned perpendicular with the front face wall 32. The centerline of the lower surface 54 is coaxial with the centerline of the opening 37 of the port 40. Wire 52 connects the block 53 with the electrical circuitry within the housing 12 through rear chamber wall 28. The block 53 is preferably made of carbon.

The diameter of opening 37 can be of such size as to accept conventional 22-, 18-, 14- or any other gauge stainless steel needles therethrough. Additionally, the device 10 may incorporate a plurality of needle receiving means so that a single device 10 may be used to destroy a number of different style and diameter needles, such as, for example, intravenous, butterfly and catheter placement needles.

The optional waste collection means 16 is disposed beneath and in communication with the burn chamber 14 and comprises a tray 70 that is slidably removable from housing 12 as shown in FIG. 2. The tray 70 receives therein the melted needles that result from the operation of the device 10.

The tray 71 is retained within the housing 12 by means of a locking arm 72 that is operatively connected to the keylock 74. The keylock 74 is a safety feature, ensuring that only authorized personnel open the device 10. By turning a key (not shown), the user turns the key lock 74 and releases the locking arm 72 and allows the tray 70 to be removed.

A toggle switch 75 is mounted to the front face 32 of the housing 12. An LED light 76 is also positioned on the front face 32 and when switch 75 is moved to the "ON" position the light is illuminated. The power source is normally a 12-volt battery 78 that is rechargeable through charging opening 80 in side surface 18. The battery 78 is housed on the rear of the burning chamber 14 and is contained by rear chamber wall 28, battery side walls 85, battery rear wall 87, battery top wall 88, and battery bottom wall 89. A second LED light, not shown, may be provided to indicate that the charging circuit is in use. A conventional breaker can be used in place of the fuse.

Figure 5:
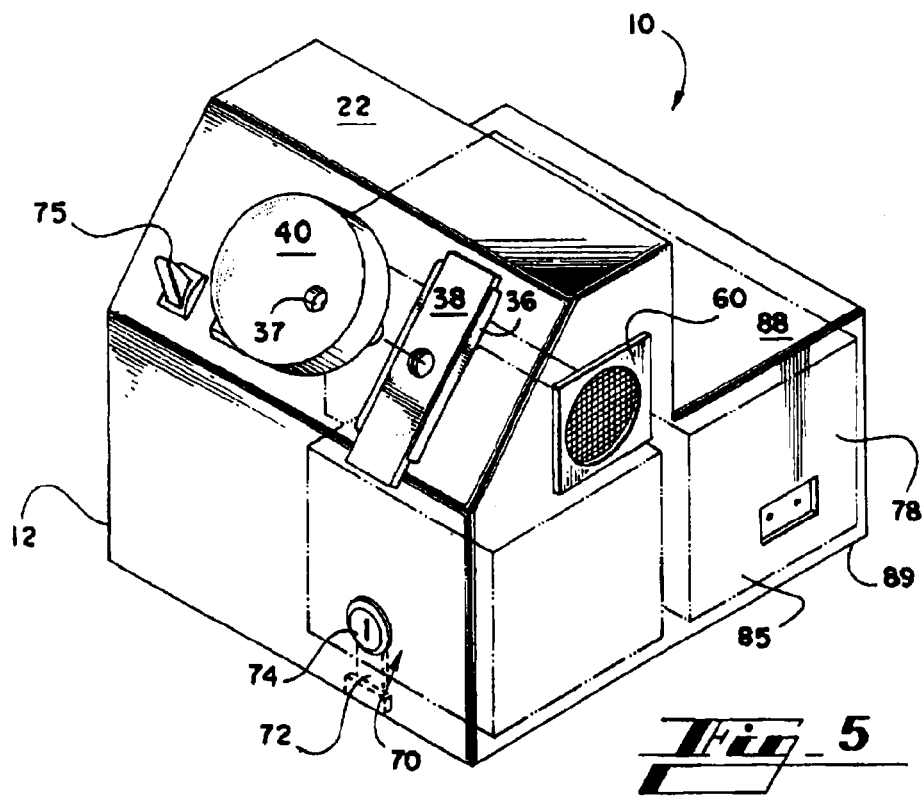
FIG. 5 is a perspective view of a first alternative embodiment of FIG. 1.

An electric fan 60 shown in FIG. 5 is mounted to one of o the side chamber walls 25, adjacent to the tray 70. Wire 51 connects the fan with the electrical circuitry within the housing 12 through the rear chamber wall 28. Thus, the fan is activated when the switch 75 is moved to the "ON" position.

Operation

To operate the device 10, the user flips the switch 74 to the "ON" position, which in turn allows electricity to flow from battery 78 to the first electrical contact 33 and to block 53. The light 76 will also be illuminated, indicating that the device 10 is operative. The fan 60 will also be energized.

The user inserts the needle 50 into the port 40 until the shoulder 46 engages the port. When the length of the needle 50 is enclosed within the burning chamber 14, the user causes the length of the needle to contact the block 53. Because the shoulder portion 46 is in contact with the first electrical contact 33, the needle portion 42 then acts as a jumper between contact 33 and block 53, closing the circuit and melting the needle portion 42. The majority of the metal needle portion 46 melts off of the needle 50 and falls into the tray 70.

Once the needle 50 is sealed, the user withdraws the needle 50 from the device 10. Another needle 50 may be inserted into the device 10 or the device 10 can be de-energized by turning the switch 75 to the "OFF" position. The light 76 will then go off, indicating that the device 10 is inoperative.

Waste material in tray 70 can be removed by turning the keylock 74 to the "UNLOCK TRAY" position. The contents of the tray 70 are sterile, so they can be disposed of as normal waste materials. The tray 70 will contain no contaminated metal so incidents of infection will be eliminated. The remaining body portion 48 of the needle 50 can be recycled as sterilized plastic.

First Alternative Embodiment

Figure 6:
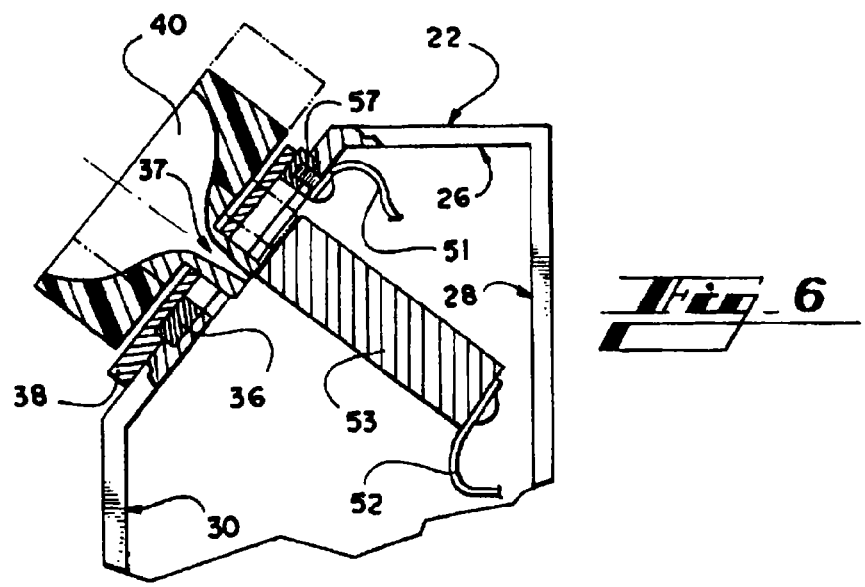
FIG. 6 is a partial cross-section view of the device of FIG. 5.

As seen more clearly in FIGS. 5 and 6, the first alternative embodiment is similar to the device shown in FIGS. 1 through 4 except that the first electrical contact 33 is mounted on the front face wall 32 of the burning chamber 14 and comprises a fixed plate 36. A sliding plate 38 is in sliding relation within the fixed plate 36. A conical shaped port 40 is threadably mounted on the sliding plate 38. The port 40 tapers downwardly through the sliding plate 38 which exits the face of fixed plate 36. The fixed plate 36 has an opening 37 centrally disposed therethrough. The port 40 and opening 37 are dimensional to receive the metal needle portion 42, the neck portion 44, shoulder portion 46, and body portion 48 of a hypodermic needle 50. Wire 51 connects the fixed plate 36 with the electrical circuitry within housing 12 through rear chamber wall 28.

The second electrical contact 51 is a block 53 and is structured in the same manner described above for the device shown in FIGS. 1 through 4.

In operation, the first alternative embodiment operates initially similar to the embodiment described above. To operate the device 10, the user flips the switch 74 to the "ON" position, which in turn allows electricity to flow from battery 78 to the first electrical contact 33 and to block 53. The light 76 will also be illuminated, indicating that the device 10 is operative. The fan 60 will also be energized.

The user inserts the needle 50 into the port 40 until the shoulder 46 engages the port. When the length of the needle 50 is enclosed within the burning chamber 14, the user causes the length of the needle to contact the block 53. Because the shoulder portion 46 is in contact with the first electrical contact 33, the needle portion 42 then acts as a jumper between contact 33 and block 53, closing the circuit and melting the needle portion 42. The majority of the metal needle portion 46 melts off of the needle 50 and falls into the tray 70.

To seal off any remaining portion of the needle, the user moves the body of the syringe upwardly while shoulder 46 of the needle is flush against the port. This upward motion causes the sliding plate 38 to slide within the fixed plate 36. Any remaining metal on the needle 50 seals as it contacts solid surface of the fixed plate 36 above the opening 37 and seals the needle. While in operation, the optional fan 60 draws any unpleasant odors and smoke resulting from the molten metal out of the burn chamber and disperses the odors through a filter into the atmosphere.

Second Alternative Embodiment

A second alternative embodiment is shown in FIGS. 7 and 8. In lieu of the first electrical contact being an opening 37 on a sliding plate 38, it is contemplated that alternatively the first electrical contact comprise a pair of opposed, springloaded cylinders 90. Each of the cylinders 90 is mounted within a cylinder housing 91. The cylinder housing 91 has a chamber 92 that receives a spring 93 and the pin 90. The cylinder housings 91 are mounted in opposed relation to each other to the front face wall 32. Wires 56, 58 connect the cylinders 90 with the electric circuitry within the housing 12 through the rear chamber wall 28. The electric contact is made when pins contact the needle as it passes through the opening 37 and into the burning chamber 14.

Third Alternative Embodiment

A third alternative embodiment is shown in FIG. 9. The third alternative embodiment is similar to the preferred embodiment discussed above except for the opening 37. It is contemplated that the opening 37 may be dog-legged. The alternative embodiment in FIG. 9 has a port 40 and a stepped channel 95. The channel 95 has a first length 96 connected to a second parallel length 97. The lengths 96, 97 are not coaxial. When the needle 50 is inserted in the port 40, the needle must pass through both lengths of the channel thus better ensuring electrical contact at that point. It must be noted that the degree of offset between the first 96 and second 97 lengths of the channel 95 cannot be greater than the channel diameter. This is to enable the needle 50 to pass through the channel 95 in a direction substantially perpendicular with the front face wall 32 and to enable the length of the needle to contact the second electrical contact 52.

Fourth Alternative Embodiment

Figure 13:
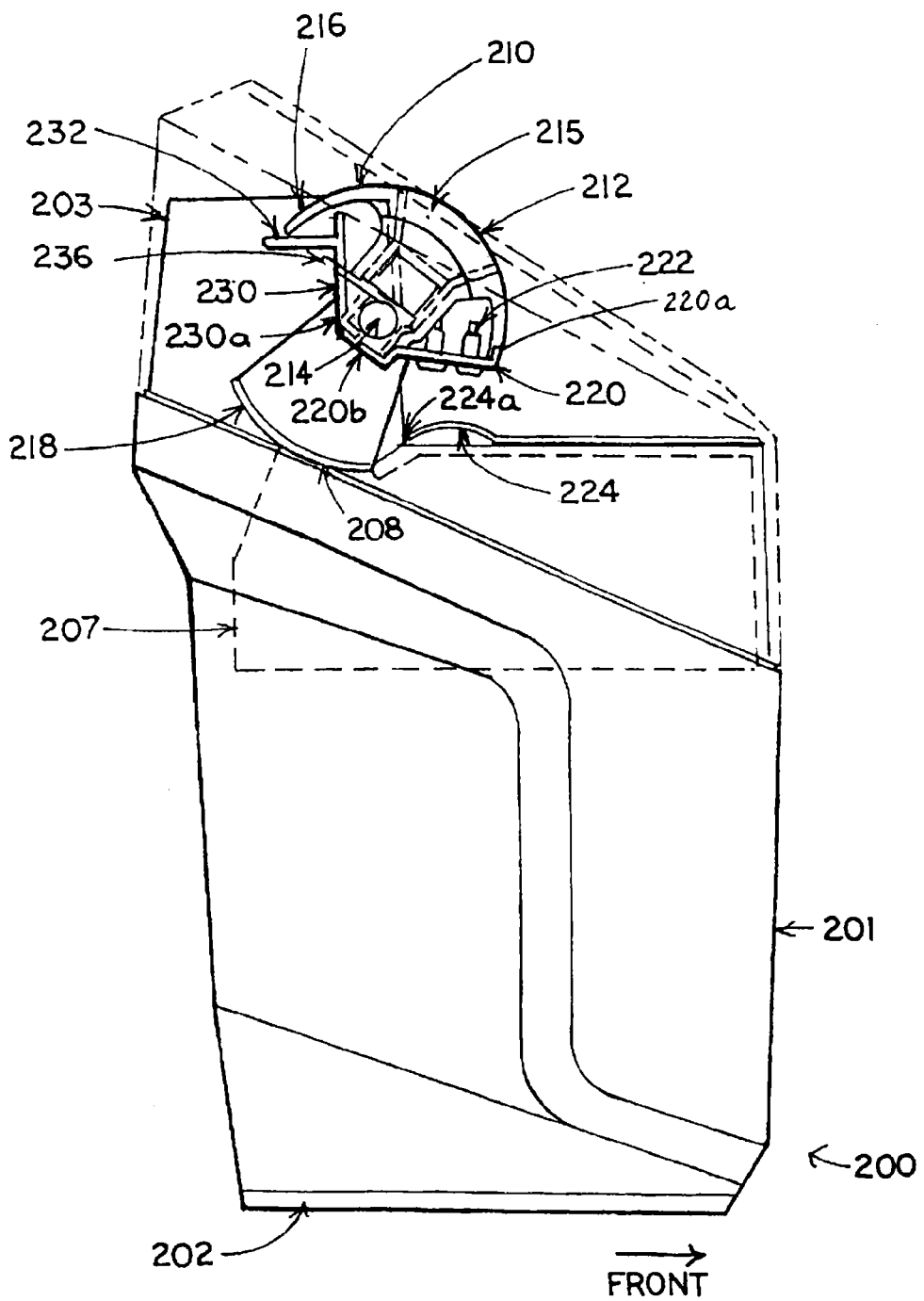
FIG. 13 is a partial cross-sectional view of a fifth alternative embodiment of the present invention, with part of the housing removed for detail.

A fourth alternative embodiment is shown in FIGS. 11-13. This alternative embodiment is directed to the bending of the remaining needle after the majority of its length has melted. The fourth alternative embodiment is similar to the preferred embodiment in that It has a housing 12, second electrical contact 52, burning chamber 14. and battery 78.

The fourth alternative embodiment; however, has a different mechanism for receiving the needle and for finishing the needle butt at the end of the melting process. The fourth alternative embodiment includes an inner disc 100 threadably mounted to the front face wall 32 of the burning chamber 14. An axle 101 extends outwardly from the center of the face of the inner disc 100. Two pins 102 extend outwardly from opposite halves of the face of the inner disc 100. A kidney shaped hole 103 is cut from the inner disc 100. An outer disc 104 is rotatably mounted on the inner disc 108 by means of the axle 101. An inner sleeve 105 is fixedly mounted to the inner surface of the outer disc 104. The kidney shaped piece 103 receives the inner sleeve 105 and enables the inner sleeve to rotate over a limited distance. A cup 106 is mounted to the outer surface of the outer disc 104. The cup supports and receives the syringe shoulder while the needle is inserted into the burning chamber 14. A pair of small, kidney shaped openings 107 are located on opposite halves of the inner face of the outer disc 104. The openings 107 receive the pins 102 mounted to the inner disc. The pins 102 provide support and enable the outer disc to rotate over a limited distance relative to the inner disc 100. The distance of rotation for the outer disc 104 is defined by the arc in the openings 107 and the kidney shaped piece 103.

In operation, the needle 50 is inserted and melted as discussed above for the preferred embodiment. After most of the length of needle has melted, any remaining needle is sealed by rotating the outer disc 104. This causes the needle 50 to bend as it contacts the outer surface of the inner disc 100.

It is to be understood that an important part of the present invention is preferred that the needle be inserted in a non-vertical orientation. The angle from the vertical can be between 10° and 90° with the more preferred angle range of between 20° and 75° with the most preferred angle range of approximately 45°.

It will be appreciated that the embodiments discussed above are the preferred embodiments, falling within the scope of the appended claims, and that various other alternative embodiments are contemplated. For example the angle of the front face wall 32 may be altered to accommodate the user. Moreover, it is contemplated that the battery 78 may be stored below the burning chamber 14 for wallmounted units.

Fifth Alternative Embodiment

A fifth alternative embodiment of the present invention is described below with reference to FIGS. 13-16. In general, this alternative embodiment includes a rotating needle carriage that receives a needle in a loading position. The needle carriage is rotated downwardly to a cut-off position. At the cut-off position, two opposing contact blades pinch the needle, which electrically connects the positive and negative terminals of a battery. Current flows through the contact blades and the portion of the needle between the contact blades, thereby melting the needle and severing the metal needle from the syringe. The severed portion of the needle then falls into a waste compartment under the contact blades. When the syringe is removed from the needle carriage, the needle carriage rotates upwardly and returns to the loading position.

Figure 14:
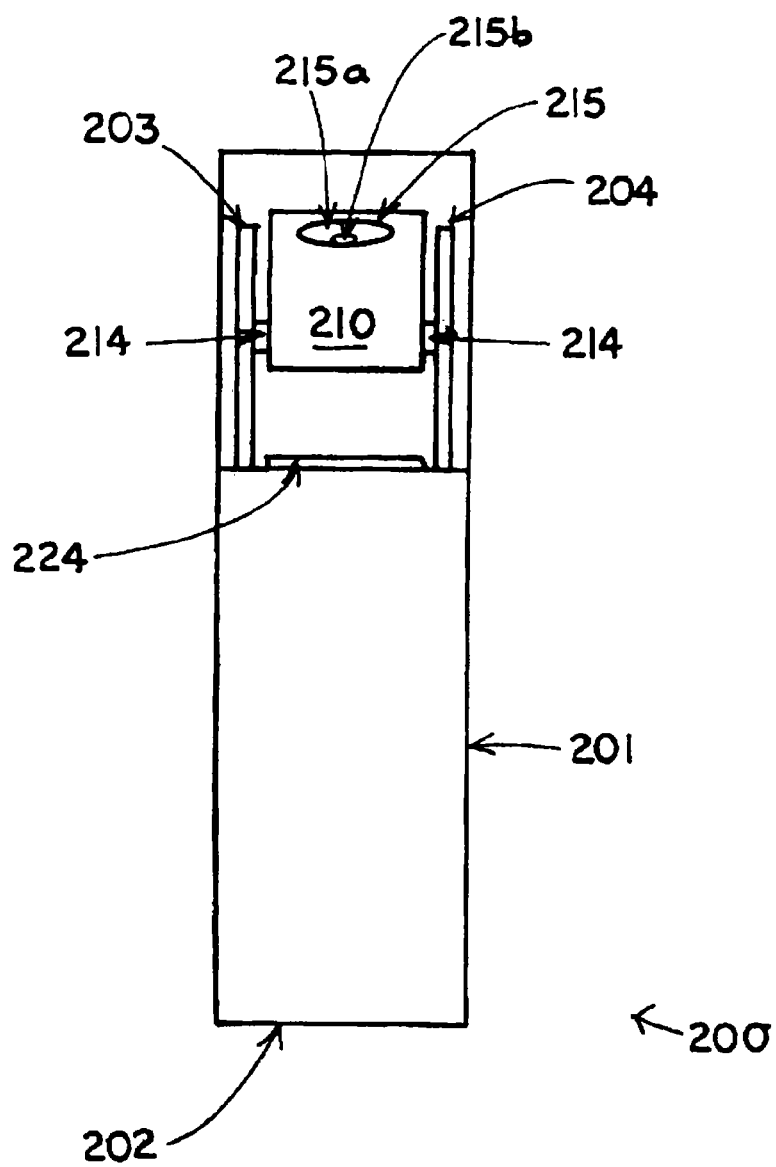
FIG. 14 is a front view of the device of FIG. 13.

The apparatus 200 of this alternative embodiment of the present invention is shown in FIG. 13. The apparatus includes a housing 201. The housing preferably includes an essentially flat bottom surface 202, thus allowing the apparatus to be plated upright on a table, countertop, or other similar surface. As is shown in FIG. 14, located near the upper portion of the apparatus are a left upper side wall 203 and a right upper side wall 204. A waste compartment 207, generally comprising a hollow chamber, is located within the housing. The upper portion of the waste compartment 207 is defined by an opening 208. A needle carriage, generally shown at 210 in FIG. 13 is rotatably connected between the upper side walls 203 and 204.

The needle carriage 210 includes a generally convex outer surface 212. Pins 214 rotatably connect the needle carriage to the upper side walls 203 and 204. A port 215 for receiving a needle is provided in the needle carriage 210. At the outermost edge of the port 215, i.e., where the port intersects the convex outer surface 212 of the needle carriage, the port includes a wide opening 215a (FIG. 14). The wide opening 215a of the port 215 allows the port to accept the neck and shoulder portions of a hypodermic syringe. The port tapers to a smaller opening 215b (FIG. 14) dimensional to receive the metal needle portion of a hypodermic syringe.

The needle carriage 210 includes an integrally formed carriage arm 216. The carriage arm 216 extends from the port 215 toward the rear of the housing 201. A door 218 is connected to the needle carriage 210 and is situated generally opposite the port 215. The door 218 is of a dimension as to entirely cover the opening 208 to the waste compartment 207 when the needle carriage is in the loading position shown in FIG. 13 and FIG. 15.

Also attached to the needle carriage is a first contact blade 220. The first contact blade 220 is formed of electrically conductive material and is secured to the lower end of the needle carriage 210, preferably by screws 222. Any other suitable means of securing the first contact blade 220 to the needle carriage 210 may be utilized instead of screws. The first contact blade 220 includes an outer edge 220a that extends toward the outer surface of the needle carriage. The first contact blade 220 also includes an inner, sharpened edge 220b that extends inwardly, away from the outer surface of the needle carriage 210.

Figure 16:
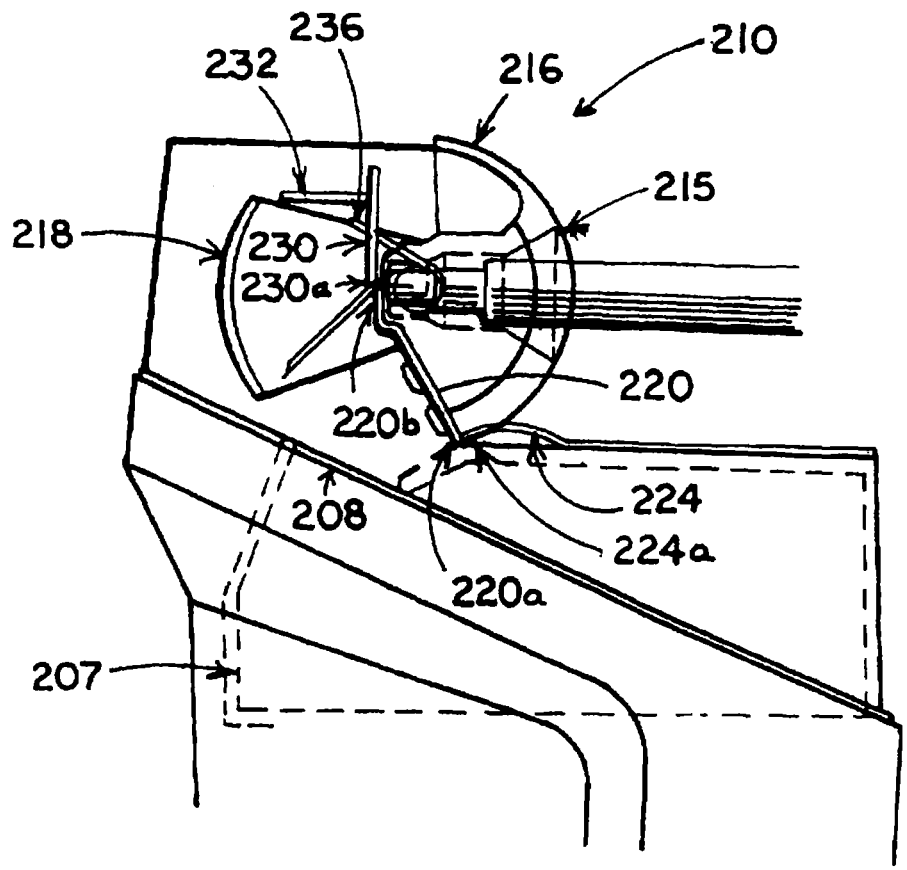
FIG. 16 is partial cross-sectional view of the device of FIG. 13 with the needle carriage in the cut-off position.

A contact strip 224, made of electrically conductive material, is connected to a portion of the housing 201 below the needle carriage 210. The contact strip 224 is located on the housing 201 in such a manner as to allow edge 224a of the contact strip to be contacted by the outer edge 220a of the first contact blade 220 when the needle carriage 210 is rotated downwardly, as shown in FIG. 16. The contact strip 224 is electrically connected to a first terminal of a battery (not shown) located within the housing 201.

Figure 15:
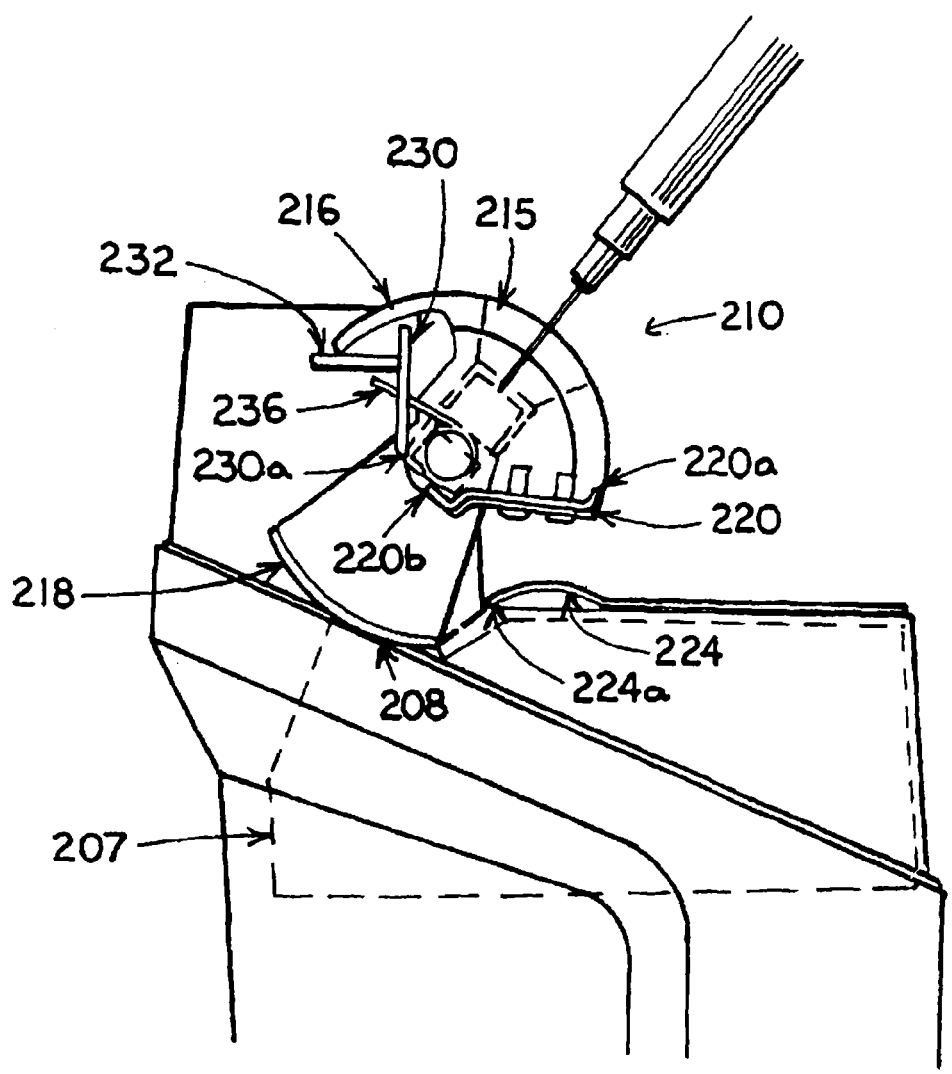
FIG. 15 is a partial cross-sectional view of the device of FIG. 13 with the needle carriage in the loading position.

A second contact blade 230 is located within the upper portion of the housing 201. The second contact blade 230 is made of electrically conductive material and is fixedly secured within the housing 201 in a generally vertical orientation. The lower edge 230a of the second contact blade 230 has a sharpened edge. The second contact blade 230 is electrically connected to a second terminal on the battery (not shown). The second contact blade 230 has a slot (not shown) therein through which one end of a torsion spring 236 may be situated. The location and orientation of the torsion spring 236 is shown in FIG. 15. The other end of the torsion spring 236 is fixedly secured within the housing 201. The torsion spring 236 provides constant pressure against the second contact blade 230 to maintain the needle carriage 210 in the loading position in the absence of any downward pressure. Connected near the upper edge of the second contact blade 230 is a carriage stop 232.

In operation, a hypodermic syringe is inserted, needle first, into the port 215 in the needle carriage 210 with the needle carriage at the loading position, as shown in FIG. 15. The needle is fully inserted until the neck and shoulder portions of the syringe contact wide opening 215a of the port 215 and can be inserted no further. When the needle is fully inserted, the needle passes between the sharpened edges 220b, 230a of the first and second contact blades 220 and 230, respectively.

With the needle remaining fully inserted, the syringe is moved downward so that the needle carriage 210 is rotated downwardly to the cut-off position, seen in FIG. 16. Preferably, the angular distance between the loading and cut-off positions is approximately 60°. The torsion spring 236 applies pressure on the needle carriage 210 to maintain it in the loading position. However, rotation of the needle carriage 210 is caused when sufficient downward pressure is alerted on the needle carriage to overcome the resistant force exerted by the torsion spring 236. Downward pressure is exerted on the needle carriage 210 through the neck and shoulder portions of the syringe by the person holding the syringe in the port. As the needle carriage is 10 rotated downwardly, the needle is prevented from rotating by contact with the sharpened edge 230a of the second contact blade 230. Thus, the metal portion of the needle is bent near the base of the needle, as seen in FIG. 16.

When the needle carriage is rotated downwardly to the cut-off position, as seen in FIG. 16, the outer edge 220a of the first contact blade 220 contacts the contact strip 224 and the inner, sharpened edge 220b of the first contact blade 220 contacts the needle. Therefore, when the needle carriage is rotated to the cut-off position, an electrical circuit is formed by the battery (not shown), the contact strip 224, the first contact blade 220, the metal needle, and the second contact blade 230. Electrical current flowing from the battery through the circuit is of such an amperage as to melt the metal portion of the needle between contact blades 228 and 230. A slight additional downward rotation of the needle carriage 210 causes the sharpened edges of the first and second contact blades to pinch the metal needle, shearing the needle at the pinch point.

When the needle carriage 210 is rotated to the cutoff position shown in FIG. 16, the door 218 is rotated away from the opening 208 to the waste compartment 207. Therefore, when the melted metal needle is sheared by the first and second contact blades, the severed portion of the needle falls downwardly, through the opening into the waste compartment. After the needle is melted and severed at the pinch point, the hypodermic syringe is removed from the port 215 in the needle carriage 210. Removing the syringe from the needle carriage removes the downward pressure on the needle carriage. With no downward pressure on the needle carriage, the torsion spring 236 exerts an upward force on the needle carriage. The torsion spring therefore causes the needle carriage 210 to rotate upwardly to the loading position. Rotation of the needle carriage 210 is halted at the loading position by the carriage stop 232, which contacts the carriage arm 216 to prevent any further upward rotation of the needle carriage. When the needle carriage 210 is at the loading position, the door 218 is situated over the opening 208 to the waste compartment 207, thereby ensuring that the severed needles remain in the waste compartment.

Sixth Alternative Embodiment

A sixth alternative embodiment is described below with reference to FIGS. 17-19. The advent of hypodermic syringes in a pen-type delivery system has simplified many uses for hypodermic syringes, such as the delivery of insulin. The pen-type devices are generally made to fit in a shirt pocket, pocketbook, purse, or the like. They can be made to deliver a single dose of a particular medicament, multiple doses, and/or doses of varying volume. While there are many manufacturers of the pen-type devices, they generally all provide a needle, a storage reservoir, a delivery means for the medication, and may include a measuring capability for varying the volume of medication dispensed. As such, the pen-type devices have similar dimensional characteristics, regardless of the particular manufacturer. Given the use to which the pen-type hypodermic syringe is directed, i.e., storing multiple small, or single large doses of a particular medication, the overall outside diameter of such devices is typically greater than a conventional single-dose hypodermic syringe. As such, pen-type devices are too large to be received by port 215. This situation is addressed by the sixth alternative embodiment.

The sixth alternative embodiment is designed to accommodate the dimensions of pen-type hypodermic syringes and to accomplish the electrical destruction and removal of the needle. Where components of this embodiment are the same as the fifth alternative embodiment, the same description of the parts and the same numerals are used to identify the components. As shown in FIG. 17, a port 715 is provided in the needle carriage 210. At the outermost edge of the port 715, i.e., where the port intersects the convex outer surface 212 of the needle carriage, the port includes a wide opening 715a, which is wider than opening 215a, shown and described in conjunction with the previous (fifth) embodiment. This wider opening 715a of the port 715 allows the port to accept the neck and shoulder portion of a pen-type hypodermic syringe 777. The opening 715a has a dimension sufficient to accept the neck and shoulder portion, whether the exemplary pen-type hypodermic syringe is round or multifaceted. The port tapers to the same smaller opening 215b (FIG. 14), dimensional to receive the metal needle of the pen-type hypodermic syringe.

Figure 17:
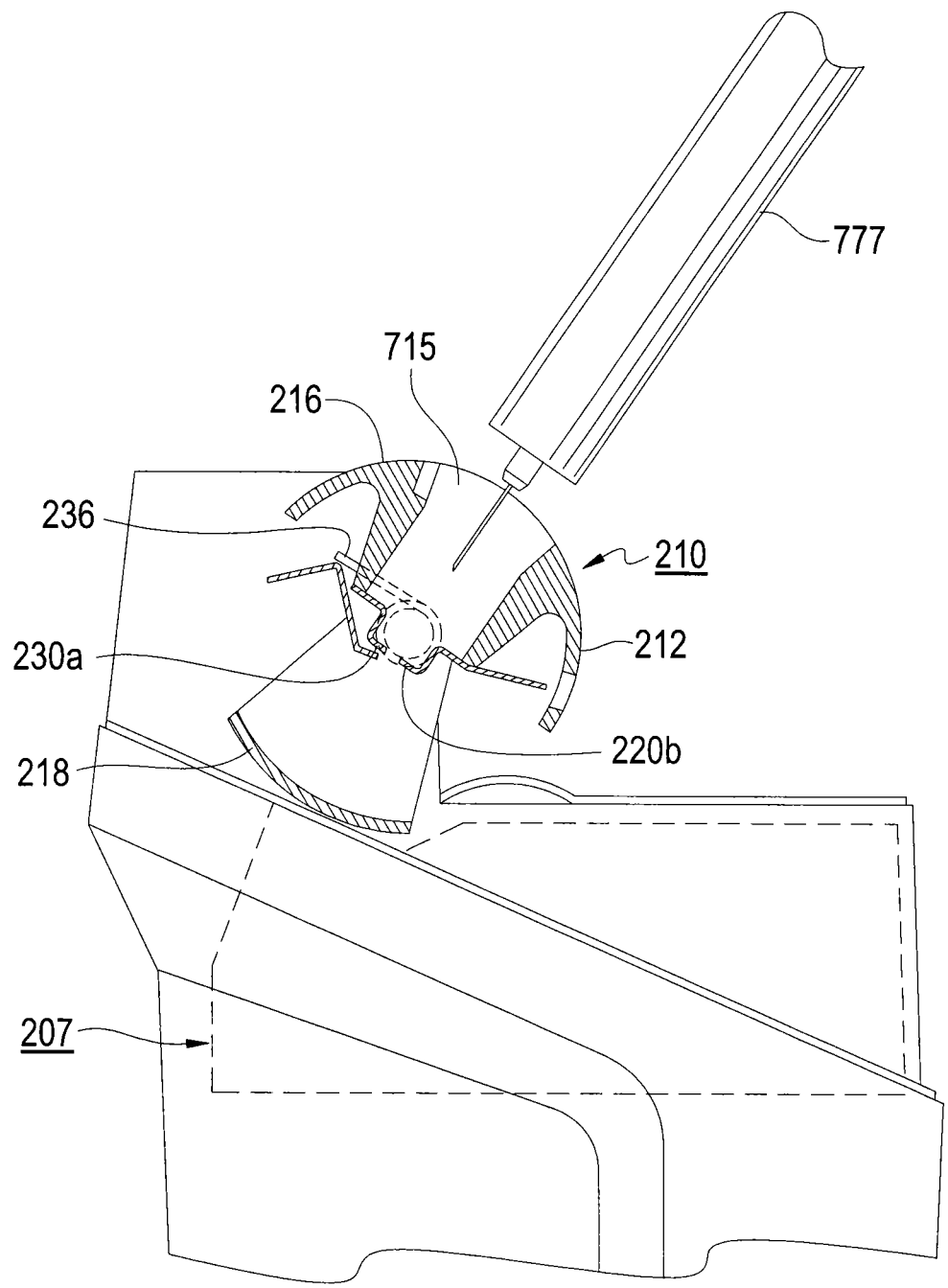
FIG. 17 is a partial, cross-sectional view of a sixth alternative embodiment with the needle carriage in the loading position.

Once the pen-type syringe 777 is inserted into port 715 as shown in FIG. 17, the operation of the needle carriage 210 is the same as described above in relation to the fifth alternative embodiment. With the pen-type syringe and needle fully inserted, the needle passes between the sharpened edges 220b, 230a of the first and second contact blades 220 and 230, respectively.

Figure 18:
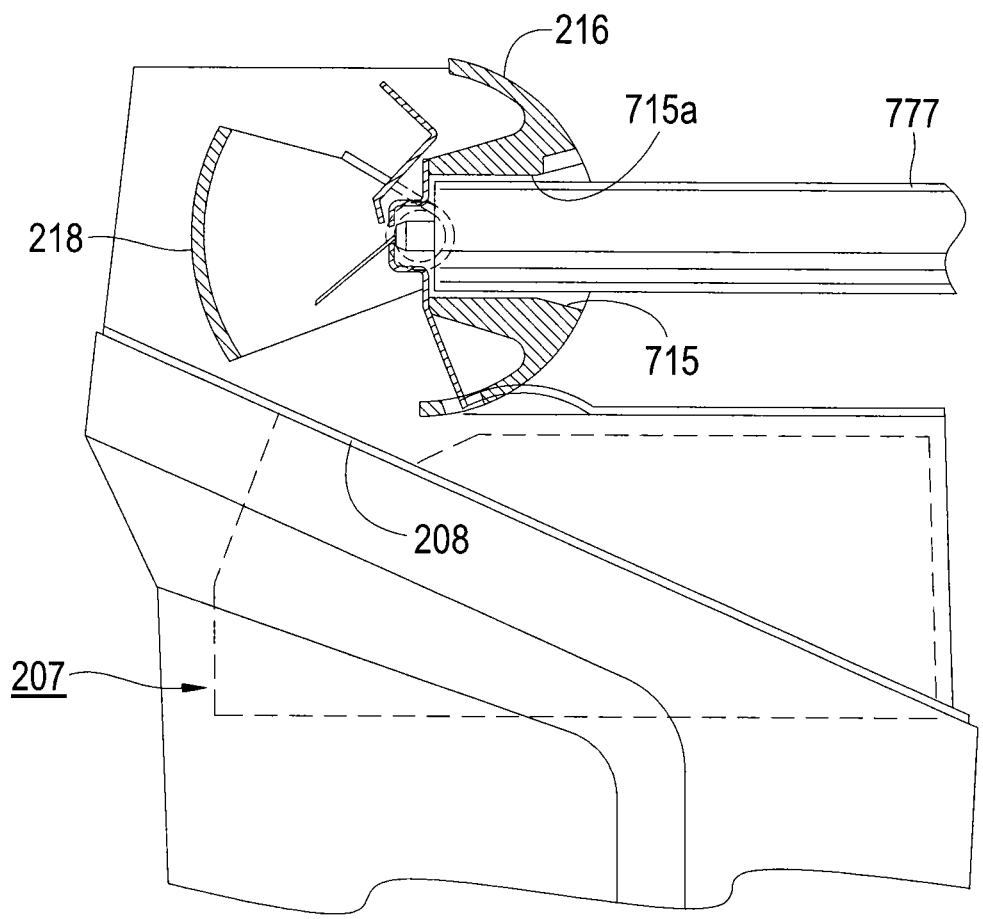
FIG. 18 is a partial, cross-sectional view of the device shown in FIG. 17, with the needle carriage in the cut-off position.

With the needle remaining fully inserted, the syringe is moved downward so that the needle carriage 210 is rotated downwardly to the cut-off position, seen in FIG. 18. Preferably, the angular distance between the loading and cut-off positions is approximately 60°. A torsion spring 236 applies pressure on the needle carriage 210 to maintain it in the loading position. However, rotation of the needle carriage 210 is caused when sufficient downward pressure is exerted on the needle carriage to overcome the resistant force exerted by the torsion spring 236. Downward pressure is exerted on the needle carriage 210 through the neck and shoulder portions of the pen-type syringe by the person holding the syringe in the port 715. As the needle carriage is rotated downwardly, the needle is prevented from rotating by contact with the sharpened edge 230a of the second contact blade 230. Thus, the metal portion of the needle is bent near the base of the needle as seen in FIG. 18.

When the needle carriage is rotated downwardly to the cut-off position, as seen in FIG. 18, the outer edge 220a of the first contact blade 220 contacts the contact strip 224 and the inner, sharpened edge 220b of the first contact blade 220 contacts the needle. Therefore, when the needle carriage is rotated to the cut-off position, an electrical circuit is formed by the battery (not shown), the contact strip 224, the first contact blade 220, the metal needle, and the second contact blade 230. Electrical current flowing from the battery through the circuit is of such an amperage as to melt the metal portion of the needle between contact blades 220, 230. A slight additional downward rotation of the needle carriage 210 causes the sharpened edges of the first and second contact blades to pinch the metal needle, shearing the needle at the pinched point.

When the needle carriage 210 is rotated to the cut-off position shown in FIG. 18, the door 218 is rotated away from the opening 208 to the waste compartment 207. Therefore, when the melted metal needle is sheared by the first and second contact blades, the severed portion of the needle falls downwardly, through the opening into the waste compartment.

After the needle is melted and severed at the pinch point, the pen-type hypodermic syringe is removed from the port 715 in the needle carriage 210. Removing the syringe from the needle carriage removes the downward pressure on the needle carriage. With no downward pressure on the needle carriage, the torsion spring 236 exerts an upward force on the needle carriage. The torsion spring therefore causes the needle carriage 210 to rotate upwardly to the loading position. Rotation of the needle carriage 210 is halted at the loading position by the carriage stop 232, which contacts the carriage arm 216 to prevent any further upward rotation of the needle carriage. When the needle carriage 210 is at the loading position, the door 218 is situated over the opening 208 to the waste compartment 207 thereby ensuring that the severed needles remain in the waste compartment.

Seventh Alternative Embodiment

Figure 19:
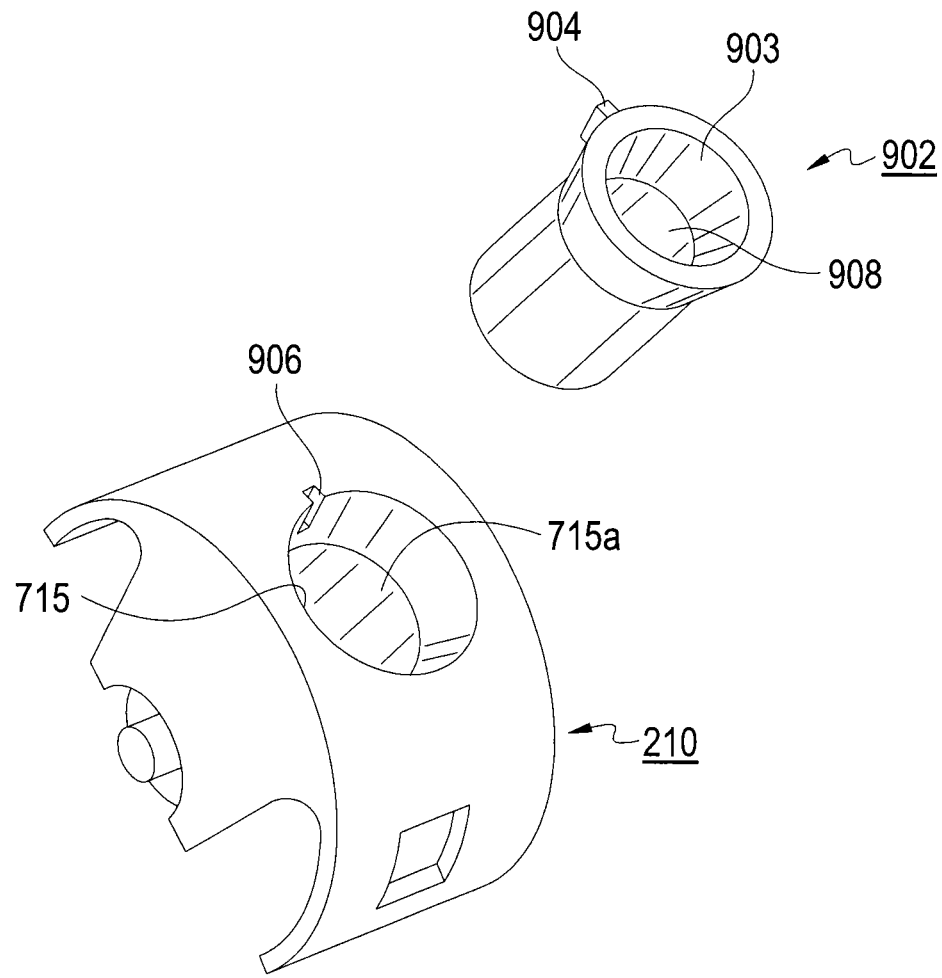
FIG. 19 is an exploded perspective view of a seventh alternative embodiment of the needle carriage of the device shown in FIG. 17, showing the large port and insert.
Figure 20:
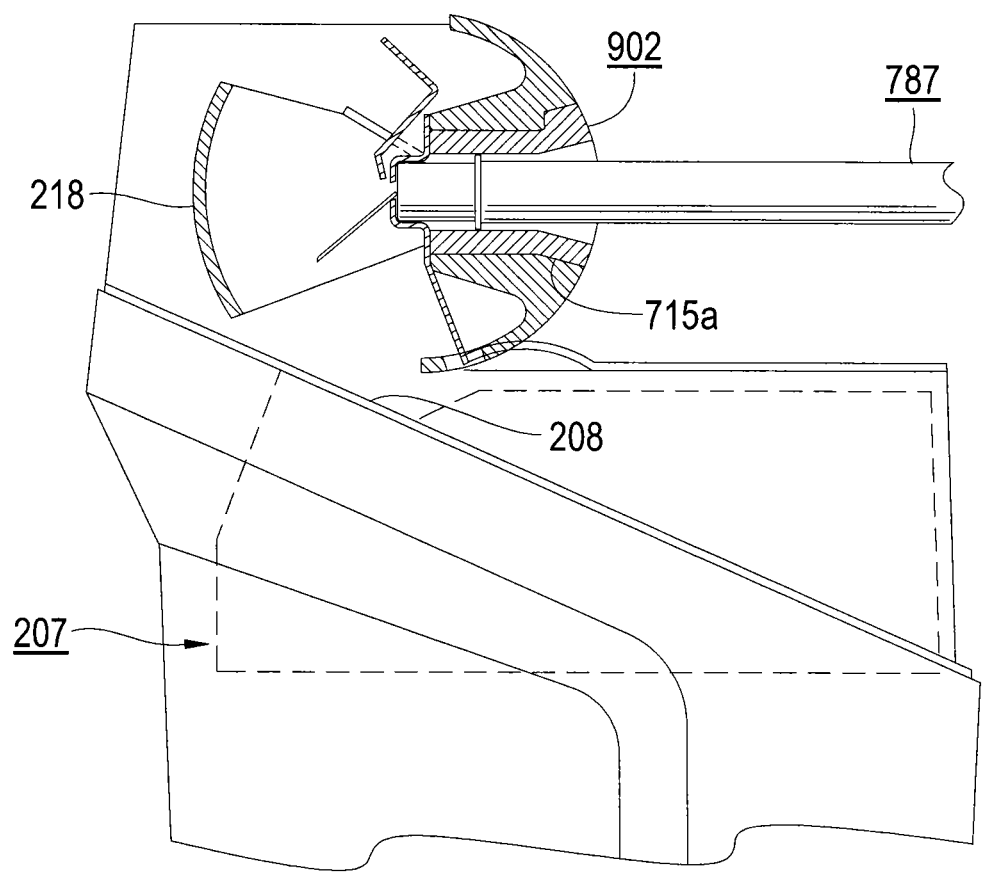
FIG. 20 is a partial cross-sectional view of the needle carriage with the insert in place for use with a conventional hypodermic syringe.

A seventh alternative embodiment of the present device is shown in FIG. 19 and FIG. 20. As described hereinabove, with reference to the sixth alternative embodiment, the needle carriage 210 of FIG. 17 has a relatively wide port 715 that is designed to accept the neck and shoulders of a pen-type hypodermic syringe. If a conventional hypodermic syringe is used and has to be destroyed, the wide opening 715 will accept the much smaller conventional hypodermic syringe as well as the larger pen-type hypodermic syringe. However, the smaller conventional syringe would be subject to a significant amount of play with the wider opening, which could possibly lead to some difficulty in use. To alleviate any such concerns, an insert 902 is provided. The insert has a slightly smaller dimension than the dimension of the port 715. This allows insert 902 to nest inside port 715, with perfect alignment being assured by the provision of a key 904 which is received in a slot 906 formed in the wide opening 715a of the port 715. Additional or alternate alignment means can also be utilized, or none at all, with alignment simply assured due to the nesting of the insert in the port 715. With the insert in place, the interior dimension 908 of insert 902 allows the port 903 to accept the neck and shoulder portion of a conventional hypodermic syringe 787. The insert is easily removed and replaced, allowing the modified device to be used with hypodermic syringes having a variety of outer dimensions, while ensuring their safe disposal. The operation then proceeds as described hereinabove with reference to the device of the sixth alternative embodiment and FIGS. 17 and 18.

From the foregoing it will be appreciated that the disclosed embodiments of the present invention overcome the drawbacks of the prior art described hereinabove. From the description of the embodiments herein, equivalents of the embodiments shown therein will suggest themselves to those At least the following is claimed:

1. An apparatus for removing the needle portion of a pen-type hypodermic syringe comprising:
   a housing;
   a needle carriage for receiving a needle in a loading position, said needle carriage being rotatably connected to the housing from the loading position to a cut-off position, the needle carriage including a wide diameter port for accepting a pen-type hypodermic syringe, said syringe having a circumference and said port having a circumference greater than said syringe;
   a first contact blade connected to the needle carriage; and
   a second contact blade secured within the housing;
   wherein said needle carriage and said contact blades are oriented such that when said needle carriage is rotated from the loading position to the cut-off position, the first and second contact blade each contact the needle.

2. The apparatus of claim 1 wherein the first and second contact blades sever a portion of the needle when the needle carriage is rotated to the cut-off position.

3. The apparatus of claim 2 further comprising a waste compartment located within the housing for receiving the severed portion of the needle, the upper portion of the waste compartment having an opening located generally beneath the needle carriage.

4. The apparatus of claim 3 further comprising a door connected to the needle carriage, wherein said door is of a dimension to cover the opening to the waste compartment when the needle carriage is in the loading position.

5. The apparatus of claim 4 wherein said door does not cover the opening to the waste compartment when the needle carriage is in the cut-off position.

6. The apparatus of claim 1 wherein the second contact blade prevents the movement of a portion of the needle, thus causing bending of the needle when the needle carriage is rotated from the loading position to the cut-off position.

7. The apparatus of claim 1 further comprising:
   an electrically conductive contact strip secured to the housing such that the first contact blade contacts the contact strip when the needle carriage is in the cut-off position; and
   a battery, the first terminal of which is connected to the contact strip and the second terminal of which is connected to the second contact blade.

8. The apparatus of claim 7 wherein the battery provides sufficient current to melt a portion of the needle when the needle carriage is in the cut-off position.

9. The apparatus of claim 1 further comprising a torsion spring connected to the housing, wherein the torsion spring provides pressure against the needle carriage to maintain the needle carriage in the loading position in the absence of a rotational force applied to the needle carriage.

10. The apparatus of claim 1 wherein the wide port in the needle carriage includes a reduced interior diameter insert for receiving the neck and shoulder portions of a conventional hypodermic syringe.

11. The apparatus of claim 1 wherein the angular distance between the loading position and the cut-off position is approximately 60 degrees.

12. A method for removing the needle portion of a pen-type hypodermic syringe, comprising the steps of:
   (a) providing a needle carriage having a port with a wide diameter sufficient to accept a neck and shoulder portion of a pen-type hypodermic syringe said syringe having an outer periphery and said port having an outer periphery larger than the periphery of said syringe;
   (b) inserting a needle into the needle carriage in a loading position, the needle carriage being rotatably connected to a housing;
   (c) rotating the needle carriage from the loading position to a cut-off position;
   (d) causing a first contact blade and a second contact blade to contact the needle when the needle carriage is in the cut-off position;
   (e) causing an electrical current to pass through the first contact blade, the needle, and the second contact blade to melt the needle; and
   (f) severing a portion of the needle with the first and second contact blades.

13. The method of claim 12 further comprising the step of retaining the severed portion of the needle in a waste compartment.

14. The method of claim 13 wherein the opening to the waste compartment is covered by a door connected to the needle carriage when the needle carriage is in the loading position and is not covered by the door when the needle carriage is in the cut-off position.

15. The method of claim 12 wherein during the rotating, step, the second contact blade prevents the movement of a portion of the needle thus causing bending of the needle when the needle carriage is rotated from the loading position to the cut-off position.

16. The method of claim 12 wherein the electrical current is provided by a battery, the first terminal of which is connected to a contact strip that contacts the first contact blade when the needle carriage is rotated to the cut-off position and the second terminal of which is connected to the second contact blade.

17. The method of claim 12 wherein the needle carriage includes a wide diameter port and a reduced diameter insert for receiving the neck and shoulder portions of a conventional hypodermic syringe.

18. The method of claim 12 wherein the angular distance between the loading position and the cut-off position is approximately 60 degrees.

19. The method of claim 12 wherein the inserting step includes inserting the syringe needle into a port in the needle carriage such that the neck and shoulder portions of the syringe contact the port.

20. The method of claim 19 wherein the rotating step is performed by exerting downward pressure on the needle carriage through the neck and shoulder portions of the syringe.

21. An apparatus for removing the needle portion of a syringe comprising:
   a pen-type hypodermic syringe having a neck and shoulder portion that are wider in diameter than a conventional hypodermic syringe;
   a housing;
   a needle carriage for receiving a needle in a loading position, said needle carriage being rotatably connected to the housing from the loading position to a cut-off position, the needle carriage including a wide diameter port for accepting a pen-type hypodermic syringe, said port having a diameter greater than the diameter of said syringe;
   a first contact blade connected to the needle carriage; and
   a second contact blade secured within the housing;
   wherein said needle carriage and said contact blades are oriented such that then said needle carriage is rotated from the loading position to the cut-off position, the first and second contact blade each contact the needle.

22. The apparatus of claim 21 and including an insert having an outside diameter that fits inside said wide diameter port and an inside diameter that is narrower to accept the neck and shoulder portion of a conventional hypodermic syringe.

* * * * *